(12) United States Patent
Yoshida et al.

(10) Patent No.: US 7,902,173 B2
(45) Date of Patent: Mar. 8, 2011

(54) COMPOUND SELECTED FROM SULFATED CELLULOSE AND SALTS THEREOF AND DERMATITIS THERAPEUTIC AGENT

(75) Inventors: Naoyuki Yoshida, Tokyo (JP); Kazushi Ishida, Kanagawa (JP); Shuji Sasaki, Kanagawa (JP); Takuo Ikeda, Kanagawa (JP); Jun Hiraki, Tokyo (JP); Shigeyuki Aoyama, Kumamoto (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 74 days.

(21) Appl. No.: 11/363,174

(22) Filed: Feb. 28, 2006

(65) Prior Publication Data
US 2006/0199784 A1  Sep. 7, 2006

(30) Foreign Application Priority Data
Mar. 1, 2005 (JP) ................ 2005-055468

(51) Int. Cl.
 *A01N 43/04* (2006.01)
 *A61K 31/715* (2006.01)
(52) U.S. Cl. .............. 514/57; 514/861; 514/863
(58) Field of Classification Search .......... 514/57, 514/861, 863
See application file for complete search history.

(56) References Cited

U.S. PATENT DOCUMENTS
4,480,091 A  10/1984  Brewer
5,346,589 A *  9/1994  Braunstein et al. ........... 162/72

FOREIGN PATENT DOCUMENTS

| DE | 40 19 116 | 12/1990 |
| DE | 40 21 049 | 1/1992 |
| JP | 60-112708 | 6/1985 |
| JP | 8-104617 | 4/1996 |
| JP | 8-277224 | 10/1996 |
| JP | 11-335288 | 12/1999 |
| JP | 2000-178196 | 6/2000 |

OTHER PUBLICATIONS

Saake, B., Puls, J., Wagenknecht, W. (2002) Endoglucanase fragmentation of cellulose sulfates derived from different synthesis concepts. Carbohydrate Polymers, 48 (1), 7-14.*
Wickholm, K., Hult, E.-L., Larsson, T., Iversen, T., Lennholm, H. (2001) Quantification of cellulose forms in complex cellulose materials: a chemometric model. Cellulose, vol. 8, p. 139-148.*
S.E. Stringer et al., "Molecules in Focus", Int. J. Biochem. Cell. Biol., vol. 29, No. 5, pp. 709-714, 1997.
Toida Toshihiko et al., "Structure and Bioactivity of Sulfated Polysaccharides", Trend in Glycoscience and Glycotechnology, vol. 15, No. 81, pp. 29-46, Jan. 2003.
Jose L. Reissig et al., "A Modified Colorimetric Method for the Estimation of *N*-Acetylamino Sugars", J. Biol. Chem., 217, pp. 959-966, 1955.
Yasushi Hirasawa et al., "Assessing Effects of a Product Containing Crude Drugs Including Scutellaria Root, Phellodendron Bark, Coptis Rhizome and Product Containing Crude Drugs Including Lithospermum Root, Japanese Angelica Root, Sesame Oil in Atopic Dermatitis NC/Nga Mice", Pharmacometrics, 59, pp. 123-134, 2000. Full English translation of JP 2000-178196, published Jun. 27, 2000.
Robert A. Anderson et al., "Preclinical Evaluation of Sodium Cellulose Sulfate (Ushercell) as a Contraceptive Antimicrobial Agent", Journal of Andrology, vol. 23, No. 3, pp. 426-438, XP002387970, ISSN: 0196-3635, May 2002.

* cited by examiner

*Primary Examiner* — Shaojia Anna Jiang
*Assistant Examiner* — Scarlett Goon
(74) *Attorney, Agent, or Firm* — Wenderoth, Lind & Ponack, LLP.

(57) ABSTRACT

The present invention provides a compound selected from sulfated cellulose and salts thereof which can be used as an active ingredient for a cutaneous external preparation produced intending to prevent, soften, improve or cure atopic cutaneous symptoms and the like and which are excellent in a hydrolytic resistance, and dermatitis therapeutic agents and cosmetics using the same.

6 Claims, No Drawings

COMPOUND SELECTED FROM SULFATED CELLULOSE AND SALTS THEREOF AND DERMATITIS THERAPEUTIC AGENT

TECHNICAL FIELD

The present invention relates to a compound selected from sulfated cellulose and salts thereof which are excellent in a hydrolytic resistance and dermatitis therapeutic agents and cosmetics using the same. More specifically, it relates to a compound selected from sulfated cellulose and salts thereof which can be used as an active ingredient for a cutaneous external preparation produced intending to prevent, soften, improve or cure particularly atopic cutaneous symptoms, and dermatitis therapeutic agents and cosmetics using the same.

BACKGROUND ART

It is known that heparin which is a representative high molecular electrolyte originating in organisms has various physiological activities such as anticoagulant activity, antiviral activity and antiinflammatory activity (refer to, for example, Int. J. Biochem. Cell. Biol. Vol. 29, p. 709 to 714, 1997). Sulfation of many natural polysaccharides has so far been carried out as trial for obtaining substances similar to above heparin showing various physiological activities (refer to, for example, Trend in Glycoscience and Glycotechnology, vol. 15, No. 81, p. 29 to 46). Among many sulfated natural polysaccharides, particularly chondroitin sulfate which is one kind of polysulfide mucopolysaccharides is known as a representative substance similar to heparin (refer to, for example, Japanese Patent Publication No. 4362/1987). Since it has a hyaluronidaze inhibitory activity power and a cutaneous moisturizing action, it is investigated to be applied, as uses of chondroitin sulfate and sulfuric acid group-introduced derivatives thereof, to dry cutaneous diseases such as xeroderma, asteatosis and progressive cutaneous keratodermia and atopic dermatitises (refer to, for example, Japanese Patent Application Laid-Open No. 277224/1996 and Japanese Patent Application Laid-Open No. 335288/1999). Also, it is reported that sulfated polysaccharide shows an inhibitory activity of hyaluronidaze originating in *staphylococcus aureus* bacteria (refer to, for example, Japanese Patent Application Laid-Open No. 178196/2000), and possibility to apply sulfated polysaccharide to a therapeutic agent for atopic dermatitis is described. Further, investigations of hyaluronidaze activity inhibition and an antiinflammatory effect of sulfated sucrose are carried out (refer to, for example, Japanese Patent No. 2723473).

It is considered that antiinflammatory action and tissue regeneration action by hyaluronidaze activity inhibition depends on the following mechanism. Hyaluronic acid and glycosaminoglycan are decomposed by hyaluronidaze, whereby a cell surface or a supporting matrix substance is broken, and the cell is exposed. It comes to be damaged by pathogens, inflammation intermediary substances, inflammatory agents and various drugs such as antiseptic agents. It is considered that hyaluronidaze activity inhibitory agents such as sulfated saccharides accelerate regeneration of a matrix of a cell surface and a protective connection tissue by inhibiting the activity of the above enzyme and that as a result thereof, they carry out the actions of antiinflammation and tissue regeneration.

Thus, for the purpose of improving or curing atopic cutaneous symptoms and the like, sulfates of hyaluronic acid, chondroitin sulfate and dextran have so far been intensively researched with activity inhibition of hyaluronidaze being set as an index, but detailed investigations on inhibition of hyaluronidaze are not reported as far as sulfated substances of cellulose are concerned. Similarly, cases in which confirmation of efficiency of sulfated cellulose and salts thereof to atopic dermatitis is investigated in detail are not available as well. It is considered as one of the causes thereof that the structure and the molecular weight of natural cellulose are diversified and that the qaulities of sulfated cellulose and salts thereof obtained are not fixed and are liable to be changed with the passage of time by hydrolysis.

Antiinflammatory agents of a steroid base are used for therapy of atopic dermatitis in medical service sites, but the above antiinflammatory agents of a steroid base are followed with strong by-effects, and it is the existing situation that administration of steroids to patients of a mild degree is contraindicated. On the other hand, nonsteroidal antiinflammatory agents have usually a weak efficacy. Accordingly, therapeutic agents for atopic dermatitis which are not followed with by-effects and which have a satisfactory efficacy at a low concentration are desired to be developed. Also, base materials which have high safety and show a high efficacy at a low concentration are desired as well in uses of cosmetics for sensitive skin and atopic skin in order to maintain the quality of the products in terms of compositions. Further, in respect to natural materials, persons in the sites who handle medicines and cosmetics tend to demand materials originating in those other than animals from the viewpoint of the safety since BSE (bovine spongiform enoephalopathy) is generated. In particular, demanded to be developed are substances which have higher performances than those of substances similar to heparin described in The Japanese Pharmaceutical Codex and which are derived from plants originating in those other than animals.

SUMMARY OF THE INVENTION

A subject of the present invention is to provide a compound selected from sulfated cellulose and salts thereof which are produced intending to prevent, soften, improve or cure particularly atopic cutaneous symptoms and which can be used as an active ingredient for a cutaneous external preparation and are excellent in a hydrolytic resistance, and dermatitis therapeutic agents and cosmetics using the same.

The present inventors have repeated intensive researches in order to meet the subject described above. As a result thereof, they have found that a compound which is selected from sulfated cellulose obtained from crystalline cellulose and salts thereof and which has a solubility of 3 g/L or more in purified water at 20° C. shows a high hyaluronidaze inhibitory activity and a marked improving effect to atopic dermatitis as compared with existing chondroitin sulfate (heparin-analogous substance), and they have completed the present invention based on the above knowledge.

The present invention is constituted from the following items.

1) A compound which is selected from sulfated cellulose obtained from crystalline cellulose and salts thereof and which has a solubility of 3 g/L or more in purified water at 20° C.
2) The compound as described in the above item 1), wherein the crystalline cellulose has an average polymerization degree of 150 to 300.
3) The compound as described in the above item 1) or 2), which has a sulfur content of 6.5 to 19.0 wt %.
4) The compound as described in any of the above items 1) to 3), which has a weight average molecular weight of 1,000 to 200,000.

5) The compound as described in any of the above items 1) to 4), which is a sulfated cellulose calcium salt or a sulfated cellulose sodium salt.
6) A compound which is selected from sulfated cellulose obtained from crystalline cellulose and salts thereof and which has a sulfur content of 6.5 to 19.0 wt %, a weight average molecular weight of 50,000 to 80,000 and a solubility of 3 g/L or more in purified water at 20° C.
7) The compound as described in the above item 6), which is a sulfated cellulose calcium salt or a sulfated cellulose sodium salt.
8) The compound as described in any of the above items 1) to 7), wherein a concentration in which a hyaluronic acid decomposition activity of hyaluronidaze originating in a bovine testicle is inhibited by 50 % in a 0.1 mol/L acetic acid buffer solution (pH 4.0) at a temperature of 37° C. is 0.018 mg/mL or less.
9) The compound as described in any of the above items 1) to 7), which shows a dermatitis inhibitory action to a dermatitis model using an NC mouse.
10) A dermatitis therapeutic agent comprising at least one kind of the compound as described in any of the above items 1) to 9).
11) A cosmetic comprising at least one kind of the compound as described in any of the above items 1) to 9).
12) The dermatitis therapeutic agent as described in the above item 10), which is used for treating atopic dermatitis.
13) A therapeutic method for dermatitis, comprising applying the compound as described in any of the above items 1) to 9) to skin.
14) The therapeutic method for dermatitis as described in the above item 13), which is used for treating atopic dermatitis.

The compound of the present invention selected from sulfated cellulose and salts thereof is excellent in a hydrolytic resistance. A dermatitis therapeutic agent containing the above compound as an active ingredient has a stable quality and is less liable to be reduced in a high effect with the passage of time, and it is effective particularly for preventing atopic cutaneous symptoms or softening, improving or curing the symptoms thereof.

BEST MODE FOR CARRYING OUT THE INVENTION

The compound (hereinafter referred to as the sulfated cellulose compound) of the present invention selected from sulfated cellulose and salts thereof is a compound obtained by converting crystalline cellulose to an electrolyte by sulfation to provide it with a water solubility or a salt thereof. Since cellulose which is a raw material for the sulfated cellulose compound is crystalline cellulose, the sulfated cellulose compound obtained is excellent in a hydrolytic resistance, and a dermatitis therapeutic agent obtained from the above sulfated cellulose compound is less liable to be reduced in a high effect with the passage of time.

The sulfated cellulose compound of the present invention has a solubility of 3 g/L or more, preferably 15 g/L or more and less than 20 g/L in purified water at 20° C. If the solubility is 3 g/L or more, the sulfated cellulose compound of the present invention is converted to an electrolyte and provided with a water solubility, and it is effective particularly for preventing atopic cutaneous symptoms or softening, improving or curing the symptoms thereof.

It does not matter what kind of the crystalline cellulose is used for the sulfated cellulose compound of the present invention as long as the crystalline cellulose originates in plants. If it has an average polymerization degree of 150 to 300, particularly about 240, the compound which has a high crystallinity and is chemically stable is liable to be obtained, and therefore it is preferred. The sulfated cellulose compound obtained by using the above crystalline cellulose is chemically stable as well and excellent in a hydrolytic resistance, and as a result thereof, a dermatitis therapeutic agent containing the above sulfated cellulose compound as an active ingredient is less liable to be reduced in a high effect with the passage of time.

The crystalline cellulose used for the sulfated cellulose compound of the present invention is preferably a compound listed in the thirteenth revised Japanese Pharmacopoeia, and capable of being used are, for example, commercially available ones such as cellulose fine crystal (Wako Pure Chemical Industries, Ltd., Osaka city) and crystal cellulose (brand name: Ceolus, Asahi Chemical Industry Co., Ltd., Tokyo).

A weight average molecular weight of the sulfated cellulose compound of the present invention shall not specifically be restricted, and it is preferably 1,000 to 200,000, more preferably 50,000 to 80,000. The sulfated cellulose compound in which a weight average molecular weight falls in the range described above is obtained from the crystalline cellulose described above having a high crystallinity, and therefore it is chemically stable and suited as an active ingredient for a dermatitis therapeutic agent.

A method for sulfating the crystalline cellulose shall not specifically be restricted, and it can be carried, for example, in the following manner. First, crystalline cellulose is swollen by a solvent such as pyridine, dimethyl sulfoxide and dimethylformamide, and dropwise added thereto as a sulfating agent are chlorosulfonic acid, piperidine-N-sulfuric acid, a sulfuric anhydride-dimethylformamide complex, a sulfur trioxide-pyridine complex, a sulfur trioxide-trimethylamine complex and a sulfuric acid-trimethylamine complex. A use amount of the sulfating agent can optionally be selected according to a sulfation rate (or a sulfur content) of the targeted sulfated cellulose and the reaction conditions, and it is suitably added in an amount of 1.2 to 3 equivalents based on a hydroxyl group of the cellulose. The reaction is carried out, though varied depending on the solvent and the sulfating agent, at 0 to 100° C., preferably 20 to 85° C. for 0.5 to 24 hours, preferably 0.5 to 10 hours in an inert gas. After the reaction, a polymer is precipitated by adding methanol, ethanol, isopropyl alcohol, acetone or the like. Alternatively, the polymer may be precipitated by adding the reaction liquid to methanol, ethanol, isopropyl alcohol, acetone or the like. Further, distilled water may be added to terminate the reaction, and then it may be neutralized by alkali, for example, sodium hydroxide. This is filtered or centrifugalized and dissolved in distilled water, and ethanol, isopropyl alcohol, acetone or the like is added thereto to precipitate the polymer, or the solution is dropwise added to ethanol, isopropyl alcohol, acetone or the like to precipitate the polymer and dry it, whereby sulfated cellulose can be obtained. Also, an ion exchange resin column may be used to remove surplus inorganic salts, and ethanol, isopropyl alcohol, acetone or the like may be added thereto to precipitate the polymer. Alternatively, it is dissolved in distilled water and then dialyzed, and it is concentrated and dried, whereby sulfated cellulose can be obtained as well.

Sulfated cellulose can be used as well in the form of a pharmaceutically and physiologically allowable salt. It includes, for example, inorganic salts including salts of alkaline earth metals such as calcium and salts of alkaline metals such as sodium and potassium or salt forms obtained by a salt-forming reaction using amines such as cyclohexylamine. In particular, the calcium salts and the sodium salts are more preferred in terms of simplicity of the production process. Among them, the calcium salts are expected to be effective to various symptoms of dermatitis.

A sulfated cellulose calcium salt can be obtained, for example, by adding a calcium chloride aqueous solution to a sulfated cellulose aqueous solution and then neutralizing it. In this case, a concentration of the sulfated cellulose aqueous solution shall not specifically be restricted, and it is preferably 5 to 20 wt %. A concentration of the calcium chloride aqueous solution shall not specifically be restricted as well, and it is preferably the saturated aqueous solution. An amphoteric solvent of an alcohol base is preferred for depositing and settling down the sulfated cellulose calcium salt, and it is preferably methanol, ethanol and isopropyl alcohol.

A sulfur content of the sulfated cellulose compound is preferably 6.5 to 19.0 wt %, more preferably 12 to 15 wt %. If the sulfur content falls in the range described above, the marked hyaluronidaze inhibitory activity is exhibited.

The sulfated cellulose compound of the present invention can show a hyaluronidaze inhibitory activity. The hyaluronidaze inhibitory activity can be determined using, as a principle of determination, a Reissig method (J. Biol. Chem., 217, 959, 1955) obtained by improving a Morgana-Elson method. For example, a hyaluronidaze 50% inhibitory concentration can be determined by a method described in Japanese Patent No. 3066484.

Further, an inhibitory activity of hyaluronidaze based on a difference in a sulfation degree can be measured by adding hyaluronidaze having a fixed concentration to a solution containing hyaluronic acid which is a matrix and the sulfated cellulose compounds having various sulfation degrees and then reacting them for fixed time to analyze a decomposition speed of hyaluronic acid.

In the sulfated cellulose compound of the present invention, a concentration in which a hyaluronic acid decomposition activity of hyaluronidaze originating in a bovine testicle is inhibited by 50% in a 0.1 mol/L acetic acid buffer solution (pH 4.0) at a temperature of 37° C. is preferably 0.018 mg/mL or less, more preferably 0.015 mg/mL or less. If the above concentration is 0.018 mg/mL or less, it is generally confirmed that the marked hyaluronidaze inhibitory activity is exhibited, and a high effect of the dermatitis therapeutic agent can be expected.

A medical benefit of the sulfated cellulose compound of the present invention to atopic dermatitis can be confirmed, for example, by an animal test using an NC mouse as is the case of Hirasawa et al. (Hirasawa et al., Pharmacometrics, 59, 123 to 134, 2000). An NC mouse is a model animal which naturally develops a symptom very similar to an atopic dermatitis symptom of human beings with mites and staphylococcus aureus being an antigen when it is breeded under conventional atmosphere, and it is widely used for developing atopic dermatitis therapeutic agents (CRJ Letters, 11, 1 to 8, 1998). A fixed amount of the sulfated cellulose compound of the present invention is applied onto an affected part of an NC mouse which develops the symptom at a fixed temporal interval to observe the state of the skin. The state of the skin can be rated by a score of dermatitis which is determined based on evaluation criteria in a clinical symptom of atopic dermatitis of human beings. In this case, the efficacy of the sulfated cellulose compound of the present invention can be compared with a existing chondroitin sulfate using as a control group. In the present invention, when a dermatitis inhibitory effect is shown to a dermatitis model using an NC mouse, it means that a symptom progress in dermatitis is inhibited from histopathological manifestation.

The dermatitis therapeutic agent of the present invention contains at least one kind of the sulfated cellulose compound described above as an active ingredient. A content of the sulfated cellulose compound in the above dermatitis therapeutic agent is varied depending on the form and the applied part of the dermatitis therapeutic agent, an applying method and a frequency thereof, and it can extensively be changed depending on the extent of the dermatitis. It is blended so that a content of the sulfated cellulose compound is preferably 0.001 to 5 wt %, more preferably 0.005 to 1.0 wt % based on the whole component amount of the dermatitis therapeutic agent.

The dermatitis therapeutic agent containing the sulfated cellulose compound of the present invention as an active ingredient may contain other components as long as the pharmacological effects thereof are not substantially damaged. The examples of the components contained include preservatives, stabilizing agents, moisturizing agents, fragrances and surfactants which are conventionally used for pharmaceuticals and cosmetics.

The dermatitis therapeutic agent of the present invention intends to prevent atopic cutaneous symptoms or soften, improve or cure the symptoms thereof, and it includes intentions to prevent not only atopic symptoms but also inflammations such as itching originating in sensitive skin and dry skin and allergic dermatitises, prevent degradation thereof, soften the dermatitises and treat them.

The dermatitis therapeutic agent of the present invention is used in the forms of a lotion, an emulsion and an ointment. To be specific, capable of being given are pharmaceutical preparations such as ointments, plasters, aerosols, liquid formulations, suspensions, adhesive preparations and lotions. Further, the liquid formulations and the like can be impregnated into gauzes, absorbent cottons, wound dressings and adhesive plasters and then used.

Further, the dermatitis therapeutic agent of the present invention is used in the forms of cosmetics such as a face lotion, a milky lotion and a cream.

The present application claims the priority of Japanese Patent Application No. JP 2005-55468 filed on Mar. 1, 2005. The contents of the description of this Japanese Patent Application are incorporated in the present description by reference.

EXAMPLES

The present invention shall be explained in further details, but the present invention shall not be restricted to these examples. Percentage is wt % unless otherwise described. Evaluation test methods used in the examples and the comparative examples shall be described below.

1) Solubility

The solubility was determined by measuring the weight which was dissolved in 10 mL of water at a temperature of 20° C.

2) Sulfur Content

The sulfur content was measured by an oxygen flask combustion-ion chromatograph method.

3) Weight Average Molecular Weight of the Sulfated Cellulose Compound

A weight average molecular weight of the sulfated cellulose compound was measured by a gel filtration method. That is, used were Pullulan (Pullulan Shodex Standard P-82) as a molecular weight standard, Shodex OHpak SB-804HQ as a column and a 0.2 mol/L sodium chloride solution as a moving bed, a measured substance was eluted at a flow velocity of 0.5 mL/minute. The eluate was analyzed by means of a differential refractometer to measure elution time, whereby the weight average molecular weight was determined.

4) Average Polymerization Degree of Crystalline Cellulose

An average polymerization degree of crystalline cellulose was measured by a method of a confirming test (3) described in a thirteenth revised Japanese Pharmacopoeia instruction manual (1996, published by Hirokawa Shoten) D-586 to D-589.

Synthesis of Sulfated Cellulose Calcium Salt

Synthetic Example 1

A separable flask of 3 L (liter) equipped with a thermometer, a dropping funnel, a stirring device and a nitrogen gas-introducing tube was charged with 180.0 g of crystalline cellulose (brand name: Ceolus PH-101, average polymerization degree: 242) and 160 mL of dimethylformamide, and the mixture was stirred overnight. Next, 1220.75 g of a 18%-sulfuric anhydride-dimethylformamide complex was added thereto under cooling with ice in 35 minutes, and then the reaction vessel was dipped in a constant temperature bath of 20° C. The temperature was elevated in 20 minutes to carry out reaction at 20° C. for 6 hours.

After finishing the reaction, the reaction vessel was cooled down to 5° C. with ice, and the reaction liquid was slowly thrown into 1220 mL of water in 75 minutes while cooling with ice. Subsequently, calcium hydroxide was slowly added thereto until a pH of the reaction liquid became 7. In this case, an amount of calcium hydroxide required for neutralization was 70.82 g. The precipitate produced was filtered off, and the filtrate was thrown into 20 L of isopropyl alcohol to deposit a polymer and filter it off. The filtrate was dried under reduced pressure at 40° C. for 8 hours to obtain a sulfated cellulose calcium salt. A yield of the sulfated cellulose calcium salt thus obtained was 130 g, and it had a solubility of 15 g/L in purified water of 20° C., a sulfur content of 14.0 wt % and a weight average molecular weight of 77,000.

Synthetic Example 2

A separable flask of 3.0 L equipped with a thermometer, a dropping funnel, a stirring device and a nitrogen gas-introducing tube was charged with 15.0 g of crystallized cellulose (Ceolus PH-101) and 75 mL of dimethylformamide, and the mixture was stirred at room temperature for 15 hours. Next, 337.5 g of a sulfuric anhydride having a concentration of 18.8 wt % -dimethylformamide solution was added thereto under cooling with ice, and then the reaction vessel was dipped in a constant temperature bath of 24° C. and heated in 20 minutes to carry out reaction at 24° C. for 6 hours.

The reaction vessel was cooled down to 5° C. with ice, and 375 mL of isopropyl alcohol was added thereto while cooling with ice to obtain a deposit. After stirring for 30 minutes, the precipitate was filtered off, and this was dissolved in 375 mL of ion-exchanged water which was cooled to 10° C. or lower to stir the solution for 15 minutes. Then, 104.0 g of a saturated calcium chloride aqueous solution and 750 mL of isopropyl alcohol were added thereto to deposit a precipitate. This was filtered off, and the filtrate was dried under reduced pressure at 40° C. for 8 hours to obtain a sulfated cellulose calcium salt. A yield of the sulfated cellulose calcium salt thus obtained was 40.3 g, and it had a solubility of 15 g/L in purified water of 20° C., a sulfur content of 15.4 wt % and a weight average molecular weight of 76,000.

Reaction was carried out below by the same method as in Synthetic Example 2 to obtain sulfated cellulose calcium salts of Synthetic Examples 3 to 7, except that a use amount of the sulfuric anhydride-dimethylformamide solution was changed as shown in Table 1. A solubility in purified water of 20° C., a sulfur content and a weight average molecular weight of the sulfated cellulose calcium salts obtained in Synthetic Examples 2 to 7 are shown in Table 1.

TABLE 1

| | Use amount of sulfuric anhydride-dimethylformamide solution (g) | Solubility (20° C. purified water) (g/L) | Sulfur content (wt %) | Weight average molecular weight |
|---|---|---|---|---|
| Synthetic Example 2 | 337.5 | 15 | 15.4 | 76,000 |
| Synthetic Example 3 | 108 | 3 | 6.5 | 60,000 |
| Synthetic Example 4 | 168 | 5 | 9.8 | 66,000 |
| Synthetic Example 5 | 216 | 10 | 13.1 | 72,000 |
| Synthetic Example 6 | 338 | 15 | 14.7 | 76,000 |
| Synthetic Example 7 | 360 | 11 | 19.0 | 80,000 |

Synthesis of Sulfated Cellulose Sodium Salt

Synthetic Example 8

A separable flask of 500 mL equipped with a thermometer, a dropping funnel, a stirring device and a nitrogen gas-introducing tube was charged with 15.0 g of crystallized cellulose (Ceolus PH-101) and 75 mL of dimethylformamide. Next, 163.8 g of a 19% -sulfuric anhydride-dimethylformamide complex was added thereto in 22 minutes under cooling with ice, and then the reaction vessel was dipped in a constant temperature bath of 20° C. and heated in 20 minutes to carry out reaction at 20° C. for 6 hours.

The reaction vessel was cooled down to 5° C. with ice, and 500 mL of isopropyl alcohol was added thereto while cooling with ice to obtain a deposit. After stirring for 30 minutes, the precipitate was filtered off, and this was dissolved in 200 mL of ion-exchanged water which was cooled to 10° C. or lower to stir the solution for 15 minutes. Then, a 20% sodium hydroxide aqueous solution was slowly added thereto so that a pH of the reaction liquid became 7. Subsequently, 500 mL of isopropyl alcohol was added thereto to deposit a polymer, and it was filtered off. The filtrate was dried under reduced pressure at 40° C. for 8 hours to obtain a sulfated cellulose sodium salt. A yield of the sulfated cellulose sodium salt thus obtained was 26.8 g, and it had a solubility of 180 g/L in purified water of 20° C. and a sulfur content of 13.6 wt %.

Synthetic Example 9

A separable flask of 3.0 L equipped with a thermometer, a dropping funnel, a stirring device and a nitrogen gas-introducing tube was charged with 75.0 g of crystallized cellulose (Ceolus PH-101) and 375 mL of dimethylformamide, and the mixture was stirred at room temperature for 15 hours. Next, 845.9 g of a sulfuric anhydride having a concentration of 17.7 wt % -dimethylformamide solution was added thereto under cooling with ice, and then the reaction vessel was dipped in a constant temperature bath of 20° C. and heated in 20 minutes to carry out reaction at 20° C. for 6 hours.

After finishing the reaction, the reaction liquid was thrown into 3000 mL of water, and then a 20% sodium hydroxide aqueous solution was slowly added thereto so that a pH of the reaction liquid became 7. The precipitate produced was filtered off, and 140.0 g of sodium chloride was added to the filtrate and stirred for 30 minutes. Then, the solution was thrown into 3 L of methyl alcohol to deposit a polymer, and it was filtered off. The filtrate was dried under reduced pressure at 40° C. for 8 hours to obtain a sulfated cellulose sodium salt. A yield of the sulfated cellulose sodium salt thus obtained was 128.5 g, and it had a solubility of 180 g/L in purified water of 20° C. and a sulfur content of 13.9% by weight.

Example 1

The sulfated cellulose calcium salt obtained in Synthetic Example 1 was diluted with Japanese Pharmacopoeia water for injection to prepare a dermatitis therapeutic agent in which a concentration of the sulfated cellulose calcium salt was 0.5 wt %.

Example 2

The sulfated cellulose calcium salt obtained in Synthetic Example 1 was diluted with Japanese Pharmacopoeia water for injection to prepare a dermatitis therapeutic agent in which a concentration of the sulfated cellulose calcium salt was 0.1 wt %.

Comparative Example 1

Hirudoid Soft (ointment containing sulfated chondroitin sulfate of 3 mg per 1 g, manufactured by Maruho Co., Ltd.) was used for Comparative Example 1.
Inhibitory Effect Test 1 to Progress in Dermatitis of Atopic Dermatitis Model NC Mouse:

Hairs of an NC/Nga series male mouse (Nihon SLC Co., Ltd.) were carefully shaved from a rear of a head to a backside of a cervical part and a back, and 100 μL of the samples prepared in Example 1 and Example 2 and 100 mg of the sample prepared in Comparative Example 1 were applied on the shaved part and the outside of the ear once a day over a period of 10 days by means of a plastic made-spatula. The tests were carried out for each 6 mice in the respective groups.

In all the examples, the state of the dermatitis on an outer surface of the parts on which the tested substances were applied was observed once a day after finishing applying. The dermatitises on the ear and the cervical part were rated to scores according to the following classification expressions to calculate the total score by putting the scores of the ear and the cervical part together.
0: no dermatitis
1: scurf skin peeled (dander, desquamation), reddening
2: edema
3: crust (erosion, ulcer) accounts for less than ¼ of the tested substance-applied parts
4: crust (erosion, ulcer) accounts for less than ½ of the tested substance-applied parts
5: crust (erosion, ulcer) accounts for ½ or more of the tested substance-applied parts The mice were exsanguinated under ether anesthesia to result in death on the day after finally applying the tested substance, and skins on the head, the cervical part and the back were extirpated and fixed with a 10% neutral buffer formalin liquid. The above skin tissues were subjected to paraffin embedding and cut into slices according to a conventional method to prepare hematoxylin and eosin-stained and toluidine blue-stained specimens, and diagnosis was conducted on (1) inflammatory cell infiltration, (2) fibrosis of corium, (3) flat epithelium hyperplasia, (4) erosion and (5) crust. Diagnostic criteria of the respective histopathological findings shall be shown below.

(1) Inflammatory Cell Infiltration

Cell infiltration in which lymphocyte, granulocyte and macrophage were mixed was deemed to be inflammatory cell infiltration. In respect to classification to grades, a case in which tissue destruction was not involved was classified to a low grade (+); a case in which tissue destruction was not involved but cell infiltration was observed in the whole part of the corium was classified to a middle grade (++); and a case in which tissue destruction was not involved but cell infiltration was observed beyond the corium was classified to a high grade (+++). An abnormal finding was not given to a case in which cell infiltration was observed only in the vicinity of erosion.

(2) Fibrosis of Corium

A case in which fibrosis was observed only on a surface layer of corium or a case in which change was not observed in a thickness of the corium was classified to a low grade (+); a case in which the corium was thickened due to fibrosis of the whole part of the corium was classified to a middle grade (++); and a case in which the whole part of the corium on the specimen was thickened was classified to a high grade (+++).

(3) Flat Epithelium Hyperplasia

A case in which the flat epithelium (surface layer) was obviously thickened due to hypertrophy of the cell or an increase in the cell number was classified to a low grade (+); a case in which a mammiform interstitium was involved was classified to a middle grade (++); and a case in which the specimen was observed to be thickened in the whole part was classified to a high grade (+++).

(4) Erosion

A case in which defective surface layers having a size of 1 visual field or less observed by a magnification of 200 times were observed in 2 parts or less or a case in which defective surface layers having a size of 2 visual fields or less were observed in 1 part was classified to a low grade (+); a case in which defective surface layers having a size of exceeding 2 visual fields were observed in 1 part or more was classified to a middle grade (++); and a case in which defective surface layers were observed on the whole part of the specimen was classified to a high grade (+++).

(5) Crust

A case in which the skin of less than ⅓ of the whole part was covered was classified to a low grade (+) (provided that a part of erosion was excluded).

Results obtained by observing the state of the dermatitis on the outer surface of the tested substance-applied parts are shown in Table 2. Further, the diagnostic results of (1) inflammatory cell infiltration, (2) fibrosis of corium, (3) flat epithelium hyperplasia, (4) erosion and (5) crust are shown in Table 3.

An inbred strain NC/Nga mouse used in the present tests had naturally an onset of dermatitis followed by strong pruritus on a face, an ear, an aucheno and a back in a border of an age in 7 to 8 weeks, and a cutaneous symptom thereof was deteriorated with advancing age. This dermatitis of the NC/Nga mouse followed by strong pruritus started from scratching behavior and was followed by hemorrhage, and it advanced to result in erosion of the skin and ulcer formation. Thus, the skin was dried and thickened. It is considered that these are dermatitises very similar to atopic dermatitis of human beings. Animals in which crust formation (score 4) was observed on a cervical part and a back part were used in order for the tests, and they were classified into groups so that the symptoms and the weights were uniformized.

As shown in Table 2, a reduction in the dermatitises was observed in the present tests respectively in all 6 examples (the dermatitis disappeared in one example out of them) in the dermatitis therapeutic agent prepared in Example 1, in 5 examples (the dermatitis disappeared in 2 example out of them) among 6 examples in the dermatitis therapeutic agent prepared in Example 2 and in 4 examples among 6 examples in the dermatitis therapeutic agent prepared in Comparative Example 1 until an administration period was finished. Considering that an average of the score tended to grow larger in the non-treated group (0 day after applied: 4.0, 11 days after applied: 4.5), it was considered that the above results indicated an inhibitory effect of a progress in the dermatitises. Further, as shown in Table 2, it was shown that the dermatitis therapeutic agents prepared in Example 1 and Example 2 were excellent in an inhibitory effect of a progress in the dermatitises as compared with the dermatitis therapeutic agent prepared in the comparative example.

Further, as shown in Table 3, the dermatitis therapeutic agents prepared in Example 1 and Example 2 were observed to decrease in a specimen number in which histopathological findings were observed as compared with the dermatitis therapeutic agent prepared in the comparative example. Particularly in (1) the inflammatory cell infiltration, the dermatitis therapeutic agent prepared in Example 2 was observed to significantly decrease (p<0.01, one side non-parametric Turkey's test) in a specimen number in which inflammatory cell infiltration was observed as compared with the dermatitis therapeutic agent prepared in the comparative example.

TABLE 2

| Applied days | Score average value | | | | | | | | | | |
|---|---|---|---|---|---|---|---|---|---|---|---|
| | 1 | 2 | 3 | 4 | 5 | 6 | 7 | 8 | 9 | 10 | 11 |
| Example 1 | 4.0 | 3.8 | 3.7 | 3.5 | 3.5 | 3.2 | 3.2 | 3.2 | 2.3 | 2.3 | 2.0 |
| Example 2 | 4.0 | 3.8 | 3.2 | 3.2 | 3.2 | 3.0 | 2.8 | 2.5 | 2.5 | 2.5 | 2.3 |
| Comparative Example 1 | 3.8 | 3.8 | 3.8 | 3.8 | 3.5 | 3.7 | 3.7 | 3.5 | 3.5 | 3.3 | 3.3 |

TABLE 3

| | Example 1 | Example 2 | Comparative Example 1 |
|---|---|---|---|
| (1) Inflammatory cell infiltration | | | |
| none (−) | 1 | 1 | 0 |
| low grade (+) | 4 | 5 | 2 |
| middle grade (++) | 1 | 0 | 4 |
| high grade (+++) | 0 | 0 | 0 |
| (2) Fibrosis of corium | | | |
| none (−) | 2 | 1 | 0 |
| low grade (+) | 4 | 5 | 3 |
| middle grade (++) | 0 | 0 | 3 |
| high grade (+++) | 0 | 0 | 0 |
| (3) Flat epithelium hyperplasia | | | |
| none (−) | 2 | 2 | 0 |
| low grade (+) | 4 | 4 | 6 |
| middle grade (++) | 0 | 0 | 0 |
| high grade (+++) | 0 | 0 | 0 |
| (4) Erosion | | | |
| none (−) | 5 | 3 | 4 |
| low grade (+) | 1 | 3 | 2 |
| middle grade (++) | 0 | 0 | 0 |
| high grade (+++) | 0 | 0 | 0 |
| (5) crust | | | |
| none (−) | 2 | 2 | 0 |
| low grade (+) | 4 | 4 | 6 |

(The number in the table shows a specimen number in which histopathological findings were observed.)

Examples 3 to 6 and Comparative Examples 2 and 3

Inhibitory effect test 2 to progress in dermatitis of atopic dermatitis model NC mouse The sulfated cellulose calcium salts obtained in Synthetic Examples 2 to 5 were used to evaluate an inhibitory effect to a progress in dermatitis of atopic dermatitis model NC mouse. Hirudoid Soft (containing sulfated chondroitin sulfate of 3 mg per 1 g, manufactured by Maruho Co., Ltd.) was used for Comparative Example 2, and water for injection (manufactured by Otsuka Pharmaceutical Factory Inc.) was used for Comparative Example 3.

Preparation of 2,4,6-trinitrochlorobenzene for induction 2,4,6-Trinitrochlorobenzene (manufactured by Tokyo Kasei Kogyo Co., Ltd.) 100 mg was weighed and dissolved by adding 0.4 mL of acetone (manufactured by Wako Pure Chemical Industries, Ltd.), and then a solution was prepared by adding thereto 1.6 mL of ethanol (manufactured by Wako Chemical Co., Ltd.) to prepare 2,4,6-trinitrochlorobenzene for sensitization. Olive oil (manufactured by Wako Pure Chemical Industries, Ltd.) was added to the above solution so that a final concentration was 0.8% (W/V) to prepare a 2,4,6-trinitrochlorobenzene solution for induction. This work was carried out immediately before administration under a yellow lamp using a brown glass-made vessel.

Induction of atopic dermatitis to NC mouse by 2,4,6-trinitrochlorobenzene

Hairs on an abdominal part of an NC/Nga Tnd Crj mouse (Charles River Laboratories Japan, Inc.) which reached an age in 8 weeks were shaved under anesthesia by ether by means of a hair clipper, and 0.15 mL of the 2,4,6-trinitrochlorobenzene solution for sensitization was applied on the shaved abdominal part and footpad by means of a plastic-made bar to sensitize it. Induction was carried out on the fourth day after sensitization. That is, hairs on a back part of an NC mouse which had been sensitized were shaved, and 0.15 mL of the 2,4,6-trinitrochlorobenzene solution for induction was applied on the shaved back part and right and left ears by means of a plastic-made bar. The NC mouse used in the present examples is a model mouse in which the total of a dermatitis score according to clinical dermatitis described later is 25 in n=8 in induction of the first time by the above method.

Administration:

The sulfated cellulose calcium salts prepared in Synthetic Examples 2 to 5 were dissolved in water for injection (Otsuka Pharmaceutical Factory Inc.) to prepare 0.1% (W/V) solutions. The above solutions 0.15 mL were applied on the induced part of an NC mouse by means of a plastic-made bar.

In administration, 2,4,6-trinitrochlorobenzene-induced NC mice of n=8 specimens in each group were used to apply the solutions once a day. Hirudoid Soft 100 mg for Comparative Example 2 and water for injection 0.15 mL (Otsuka Pharmaceutical Factory Inc.) for Comparative Example 3 were applied once a day in the same manner. The dermatitises on the seventh day after induction were observed, and the cutaneous symptoms of the NC mice were rated to a score according to the following. The results thereof are shown in Table 4.

In the dermatitis score, (a) essential pruritus, (b) reddening, hemorrhage, (c) edema, (d) abrasion, tissue deficit and (e) crust formation and drying were rated by no dermatitis (0 point), a low grade (1 point), a middle grade (2 points) and a high grade (3 points), and the total thereof was used. The larger total score means that an atopic symptom of the model mouse is severer.

It has been found from the results of the present examples that particularly the sulfated cellulose calcium salts having a sulfur content of 9.8% or more effectively function to the mice which stay in the middle of having an onset of an atopic symptom at the beginning of induction and which have a very low grade of the symptom.

The present examples were carried out according to precedents of Hirasawa et al. (Hirasawa et al., Pharmacometrics, 59, 123 to 134, 2000).

TABLE 4

| | | Total of dermatitis score on 7th day |
|---|---|---|
| Example 3 | Sulfated cellulose calcium salt (Synthetic Example 3, sulfur content: 6.5%) | 14 |
| Example 4 | Sulfated cellulose calcium salt (Synthetic Example 4, sulfur content: 9.8%) | 8 |
| Example 5 | Sulfated cellulose calcium salt (Synthetic Example 5, sulfur content: 13.1%) | 10 |
| Example 6 | Sulfated cellulose calcium salt (Synthetic Example 2, sulfur content: 15.4%) | 12 |
| Comparative Example 2 | Hirudoid Soft | 18 |
| Comparative Example 3 | Water for injection | 15 |

Examples 7 to 12

Activity Inhibitory Test 1 of Hyaluronidase Originating in a Bovine Testicle

The sulfated cellulose calcium salts obtained in Synthetic Examples 2 to 7 and having different sulfur contents were used to carry out an activity inhibitory test of hyaluronidase originating in a bovine testicle. Reagents used are manufactured by Wako Pure Chemical Industries, Ltd. unless otherwise described.

Six kinds of the following solutions were prepared.

Solution A: 0.1 mol/L acetic acid buffer (pH 4.0) solution (concentration: 2.83 mg/mL) of hyaluronidase (manufactured by Sigma) originating in a bovine testicle Solution B: 0.3 mol/L sodium chloride-0.1 mol/L acetic acid buffer solution (pH 4.0)

Solution C: 0.1 mol/L acetic acid buffer (pH 4.0) solution (concentration: 1.83 mg/mL) of sodium hyaluronate (manufactured by Chisso Corporation)

Solution D: 0.4 mol/L sodium hydroxide aqueous solution

Solution E: 0.8 mol/L sodium borate aqueous solution

Solution F: solution prepared by adding 1.25 mL of 10N hydrochloric acid and 98.75 mL of acetic acid to 1 g of para-dimethylaminobenzaldehyde Preparation of Test Solutions:

The solution A 0.25 mL was mixed with the solution B 0.2 mL, and the mixture was maintained at 37° C. for 20 minutes. Each 0.1 mL of aqueous solutions obtained by controlling the sulfated cellulose calcium salts obtained in Synthetic Examples 2 to 7 and having different sulfur contents to concentrations of 0.001 mg/mL, 0.01 mg/mL, 0.02 mg/mL, 0.1 mg/mL, 1.0 mg/mL and 10.0 mg/mL was added to the above solution, and the solutions obtained were left standing still in a constant temperature bath at 37° C. for 20 minutes. Further, 0.2 mL of the solution C was added thereto and left standing still in the constant temperature bath at 37° C. for 20 minutes. Next, 0.1 mL of the solution D and 0.1 mL of the solution E were added thereto, boiled for 3 minutes and then cooled down, and 3.0 mL of the solution F was added thereto and left standing still in the constant temperature bath at 37° C. for 20 minutes to prepare test solutions. An absorbance $Q_E$ of the above test solutions in 585 nm was measured with N-acetylhexosamine of a reduction end produced by decomposition of hyaluronidaze being set to an index and water being set to a control.

Preparation of Control Solution 1:

A control solution 1 was prepared in the same manner as in preparation of the test solutions described above, except that a 0.1 mol/L acetic acid buffer solution (pH 4.0) was used in place of the solution A and that purified water was used in place of the sulfated cellulose calcium salt aqueous solution. An absorbance $Q_1$ of the above control solution 1 in 585 nm was measured in the same manner as in the test solutions.

Preparation of Control Solution 2:

A control solution 2 was prepared in the same manner as in preparation of the test solutions described above, except that purified water was used in place of the sulfated cellulose calcium salt aqueous solution and that the 0.1 mol/L acetic acid buffer solution (pH 4.0) was used in place of the solution C. An absorbance $Q_2$ of the above control solution 2 in 585 nm was measured in the same manner as in the test solutions.

The hyaluronidaze activity inhibitory rates were determined according to the following equation, and the concentrations of the sulfated cellulose calcium salt and the above inhibitory rates were plotted to determine a concentration (50% inhibitory concentration) of the sulfated cellulose calcium salts obtained in Synthetic Examples 2 to 7 in which a hyaluronic acid decomposition activity was inhibited by 50%:

$$\text{Inhibitory rate (\%)} = [(Q_2 - Q_1) - (Q_E - Q_1)]/(Q_2 - Q_1)$$

Shown in Table 5 are the 50% inhibitory concentrations of the sulfated cellulose calcium salt solutions having different sulfur contents and the inhibitory rates in 0.015 mg/mL.

TABLE 5

| | Example | | | | | |
|---|---|---|---|---|---|---|
| | 7 | 8 | 9 | 10 | 11 | 12 |
| | | | Synthetic Example | | | |
| | 3 | 4 | 5 | 6 | 7 | 8 |
| Sulfated cellulose calcium salt Sulfur content (%) | 6.5 | 9.8 | 13.1 | 14.7 | 15.4 | 19.0 |
| 50% inhibitory concentration (mg/mL) | 0.013 | 0.017 | 0.013 | 0.015 | 0.015 | 0.018 |
| Inhibitory rate (%) in 0.015 mg/mL | 63.4 | 38.4 | 70.5 | 55.2 | 52.2 | 28.1 |

All of the sulfated cellulose calcium salts obtained in Synthetic Examples 2 to 7 showed a high inhibitory activity.

Example 13

Activity Inhibitory Test 2 of Hyaluronidaze Originating in a Bovine Testicle
Preparation of Test Solution:

The solution A 0.25 mL was mixed with the solution B 0.2 mL, and the mixture was maintained at 37° C. for 20 minutes as was the case with Examples 7 to 12. Each 0.1 mL of aqueous solutions obtained by controlling the sulfated cellulose sodium salt obtained in Synthetic Example 8 to concentrations of 0.001 mg/mL, 0.01 mg/mL, 0.02 mg/mL, 0.1 mg/mL, 1.0 mg/mL and 10.0 mg/mL was added to the above solution, and the solutions obtained were left standing still in a constant temperature bath at 37° C. for 20 minutes. Further, 0.2 mL of the solution C was added thereto and left standing still in the constant temperature bath at 37° C. for 20 minutes. Next, 0.1 mL of the solution D and 0.1 mL of the solution E were added thereto, boiled for 3 minutes and then cooled down, and 3.0 mL of the solution F was added thereto and left standing still in the constant temperature bath at 37° C. for 20 minutes to prepare test solutions. An absorbance $Q_E$ of the above solutions in 585 nm was measured with N-acetylhexosamine of a reduction end produced by decomposition of hyaluronidaze being set to an index and water being set to a control.

A control solution 1 and a control solution 2 were prepared in the same manner as in Examples 7 to 12.

The hyaluronidaze activity inhibitory rates were determined according to the following equation, and the concentrations of the sulfated cellulose sodium salt and the above inhibitory rates were plotted to determine a concentration (50% inhibitory concentration) of the sulfated cellulose sodium salt obtained in Synthetic Example 8 in which a hyaluronic acid decomposition activity was inhibited by 50%:

Inhibitory rate (%)=$[(Q_2-Q_1)-(Q_E-Q_1)]/(Q_2-Q_1)$

Shown in Table 6 are the 50% inhibitory concentrations of the sulfated cellulose sodium salt solutions having different sulfur contents and the inhibitory rates in 0.015 mg/mL.

TABLE 6

| | Example 13 |
|---|---|
| Sulfated cellulose sodium salt | Synthetic Example 8 |
| Sulfur content (%) | 13.6 |
| 50% inhibitory concentration (mg/mL) | 0.011 |

TABLE 6-continued

| | Example 13 |
|---|---|
| Inhibitory rate (%) in 0.015 mg/mL | 92.0 |

As shown in Table 6, the sulfated cellulose sodium salt obtained in Synthetic Example 8 showed a high inhibitory activity.

Comparative Examples 4, 5 and 6

In place of the sulfated cellulose calcium salt or the sulfated cellulose sodium salt, Hirudoid Soft (ointment containing sulfated chondroitin sulfate of 3 mg per 1 g, manufactured by Maruho Co., Ltd.; the solution of the above product was prepared calculating a component content of the ointment) which was assumed to be effective for therapy of dermatitis and moisture retention and chondroitin sulfate which was a representative compound of heparinoid assumed to have a high hyaluronidaze inhibitory activity were subjected to a hyaluronidaze activity inhibitory test by the same method as in Examples 7 to 13. The results thereof are shown in Table 7.

TABLE 7

| | Comparative Example | | |
|---|---|---|---|
| | 4 | 5 | 6 |
| | Hirudoid Soft | Chondroitin sulfate | |
| | | A | C |
| Sulfur content (%) | | 5.4 | 6.0 |
| 50% inhibitory concentration (mg/mL) | 0.06 | 0.95 | 1.75 |

That is, only ⅓ to ¼ of the inhibitory activity of the sulfated cellulose calcium salt was observed in Hirudoid Soft, and only ¹/₅₀ to ¹/₁₀₀ of the inhibitory activity thereof was observed in chondroitin sulfate. Also, only about ⅙ of the inhibitory activity of the sulfated cellulose sodium salt was observed in Hirudoid Soft, and only ¹/₅₀ to ¹/₁₀₀ of the inhibitory activity thereof was observed in chondroitin sulfate.

As apparent from Tables 5 to 7, the sulfated cellulose calcium salts having a sulfur content of 6.5 to 19.0 wt % prepared in Examples 7 to 12 show a low value of 0.018 mg/mL or less in a 50% inhibitory concentration, and they show a notable hyaluronidaze activity inhibitory effect as compared with the compounds prepared in Comparative Examples 4 to 6. Also, the sulfated cellulose sodium salt prepared in Example 13 shows a 50% inhibitory concentration of 0.011 mg/mL, and it shows a notable hyaluronidaze activity inhibitory effect as compared with the compounds prepared in Comparative Examples 4 to 6.

INDUSTRIAL APPLICABILITY

The sulfated cellulose compound of the present invention has a hyaluronidaze inhibitory activity and therefore is useful as a dermatitis therapeutic agent and a cosmetic applications. The sulfated cellulose compound of the present invention is useful particularly for preventing atopic cutaneous symptoms or softening, improving or curing the symptoms thereof.

The invention claimed is:

1. A method of treating dermatitis, comprising applying a sulfated cellulose calcium salt to skin of a patient in need thereof,
wherein the sulfated cellulose calcium salt:
is obtained from crystalline cellulose;
has a solubility of 3 g/L or more in purified water at 20° C.;
has a sulfur content of 13.1 to 15.4 wt %; and
has an inhibitory rate of hyaluronic acid decomposition activity of hyaluronidase originating in a bovine testicle at a concentration of 0.015 mg/mL in a 1 mol/L acetic acid buffer solution (pH 4.0) at a temperature of 37° C. of 52.2% or higher.

2. The method according to claim 1, wherein the dermatitis is atopic dermatitis.

3. The method according to claim 1, wherein the sulfated cellulose calcium salt has a 50% inhibitory concentration ($IC_{50}$) of hyaluronic acid decomposition activity of hyaluronidase originating in a bovine testicle of a 1 mol/L acetic acid buffer solution (pH 4.0) at a temperature of 37° C. of 0.015 mg/mL or less.

4. A method of treating dermatitis, comprising applying a sulfated cellulose calcium salt to skin of a patient in need thereof,
wherein the sulfated cellulose calcium salt:
is obtained from crystalline cellulose;
has a sulfur content of 13.1 to 15.4 wt %;
has a weight average molecular weight of 50,000 to 80,000;
has a solubility of 3 g/L or more in purified water at 20° C.; and
has an inhibitory rate of hyaluronic acid decomposition activity of hyaluronidase originating in a bovine testicle at a concentration of 0.015 mg/mL in a 1 mol/L acetic acid buffer solution (pH 4.0) at a temperature of 37° C. of 52.2% or higher.

5. The method according to claim 4, wherein the dermatitis is atopic dermatitis.

6. The method according to claim 4, wherein the sulfated cellulose calcium salt has a 50% inhibitory concentration ($IC_{50}$) of hyaluronic acid decomposition activity of hyaluronidase originating in a bovine testicle of a 1 mol/L acetic acid buffer solution (pH 4.0) at a temperature of 37° C. of 0.015 mg/mL or less.

* * * * *